United States Patent [19]

Diener

[11] E Patent Number: Re. 33,319

[45] Reissued Date of Patent: Sep. 4, 1990

[54] DISPENSER FOR PASTY COMPOSITIONS

[75] Inventor: Horst Diener, Ulm-Gogglingen, Fed. Rep. of Germany

[73] Assignee: Vita Zahnfabrik H. Rauter GmbH & Co., Bad Sackingen, Fed. Rep. of Germany

[21] Appl. No.: 309,298

[22] Filed: Feb. 13, 1989

Related U.S. Patent Documents

Reissue of:

[64] Patent No.: 4,718,570
Issued: Jan. 12, 1988
Appl. No.: 27,601
Filed: Mar. 18, 1987

[30] Foreign Application Priority Data

Apr. 5, 1986 [DE] Fed. Rep. of Germany ... 8609228[U]

[51] Int. Cl.[5] ..... B65D 51/18
[52] U.S. Cl. ..... 220/253; 222/516
[58] Field of Search ..... 220/253; 222/516

[56] References Cited

U.S. PATENT DOCUMENTS

| | | | |
|---|---|---|---|
| 3,874,580 | 4/1975 | Weatherhead, III | 220/253 |
| 3,912,128 | 10/1975 | Ziemmann et al. | 222/541 |
| 4,274,563 | 6/1981 | Otterson | 222/480 |
| 4,541,541 | 9/1985 | Hickman et al. | 220/253 |
| 4,567,995 | 2/1986 | Kreiseder et al. | 220/253 |
| 4,598,837 | 7/1986 | Kreiseder et al. | 220/253 |

*Primary Examiner*—Stephen Marcus
*Assistant Examiner*—Nova Stucker
*Attorney, Agent, or Firm*—Drucker & Sommers

[57] ABSTRACT

A dispenser for pasty compositions, especially facing material in dental technology and the like, formed as a circular box (10) being closed by a cover (30) and having a bottom (17) and a wall (16). In the peripheral area of the box cavity there is arranged a packing member (11), closing an opening (32) formed in the cover (30) when the cover (30) is in closing position. The cover (30), being guided in an endless groove (36), can be turned on the box (10). Such a dispenser can be opened and closed with one hand while the other hand handles an instrument.

28 Claims, 2 Drawing Sheets

DISPENSER FOR PASTY COMPOSITIONS

Matter enclosed in heavy brackets [ ] appears in the original patent but forms no part of this reissue specification; matter printed in italics indicates the additions made by reissue.

The invention refers to a dispenser for pasty compositions, especially facing material in dental technology and the like, formed as a circular box which is closed by a cover and having a bottom and a wall.

Up to now, dental technological facing material is packed in covered boxes the cover of which has to be removed for accessing their contents. This is troublesome to the user because of the need for using both hands to open the box, he has to lay down the instrument for applying the composition. Further, it is unfavorable for the condition of the composition that the box is left open until the end of the respective use. Since, different materials are used for dental facing, e.g. dentine compound, enamel compound and dental neck compound, it is a disadvantage that the cover with the specification of the kind of composition thereon is mostly lying on the table upside down beside the box so that its identification is not visible anymore.

It is the object of the invention to provide a dispenser that can be opened and closed with one hand only. According to the invention, this object is solved in that a packing member is arranged in the peripheral area of the box cavity, covering an opening formed in the cover when the cover is in closing position, and that the cover, being guided in an endless groove, can be turned on the box.

Thus, a boxshaped container becomes a dispenser that can be held with one hand and can be operated with the same hand for opening and closing, the other hand thus remaining free for handling a spatula or another dental technological instrument. After turning the cover for removing its opening from the box's packing member, contents of the box are ready to be dispensed, and afterwards, the box is closed again by returning the cover, therefore keeping it contents permanently dustproof and maintaining the quality of the contents in the course of time. By guiding the cover on the box by means of an endless groove, the cover is kept attached to the box in every position and can neither be misplaced or lost, indications and information on the cover thus remaining reliably assigned to the contents of the dispenser. The surface of the packing member can be employed, also, as a carrier of indication, which surface is visible in the closing position of the cover through the opening thereof.

In an advantageous embodiment of the invention, the cover is formed as a cap, and knurled ring is provided on the outer circumference of the sidewall of the cap. This knurled ring facilitates turning the cover with a finger or the thumb of the hand holding the box. At the outer circumference of the wall of the box and at the inner circumference of the sidewall of the cover cap, there are arranged an annular groove and a projection, respectively, which groove and projection engage each other and serve as a cover guide. Further, they secure the cover from being unintentionally drawn off the wall of the box.

In order to obtain a comparatively large opening of the cover, to cause the opening to successively expose the whole contents of the box upon turning the cover, and to avoid removing the cover for entirely discharging the box, an advantageous embodiment of the invention provides that the packing member and the opening are shaped as part of a circular ring, and that at the inner circumference of the packing member shaped as part of a circular ring, there is arranged a central circular packing member being surrounded by a cavity shaped as part of a circular ring. Only the cavity shaped as part of a circular ring, the radius of which substantially equals the radius of the opening in the cover, shaped as part of a circular ring, can be filled with composition and discharged via the cover opening. The center of the box, being kept closed permanently by the wall surface of the cover, is occupied by the central circular packing member, and without taking off the cover, one can entirely discharge the box only by turning the cover.

Preferably, the surfaces of the packing member, limiting the ends of the cavity, extend radially with regard to the center of the box. Thus, the volume of the cavity is enlarged. Also the side edges of the opening in the cover extend radially such that the opening is larger at the outer edge than it is at the inner edge. Therefore, when dispensing contents of the box through the opening while the cover is in its opening position, only a small surface area of the composition is exposed. Small noses at the inner surface of the cover next to the side edges of the opening cooperate with the side edges of the packing member shaped as part of a circular ring, thereby acting as stoppers that lock the closed cover in a manner that may be overcome easily.

The box may be made of plastic, while both packing members, with their surfaces substantially positioned at the level of the free edge of the box wall, are advantageously molded in the bottom of the box as hollow elevations. By this effect, plastic material is saved and the weight of the dispenser is reduced.

Since applying dental technical facing material requires a plurality of different compositions, these are advantageously combined in a set so that they are readily accessible to the user. This is achieved by the dispenser according to the invention in a quite simple manner in that the bottom of the box has its lower surface surrounded by a protruding ring, and in that the cover is provided with an upper peripheral area which fits into the ring. Thus, any desired number of dispensers can be stacked on top of each other, being secured against displacement but separable axially from each other. In such a way, selling units, e.g. of triple sets per color, can be provided, allowing clear storing and easy handling by the user.

The drawing illustrates an embodiment of the invention.

Figure 1:
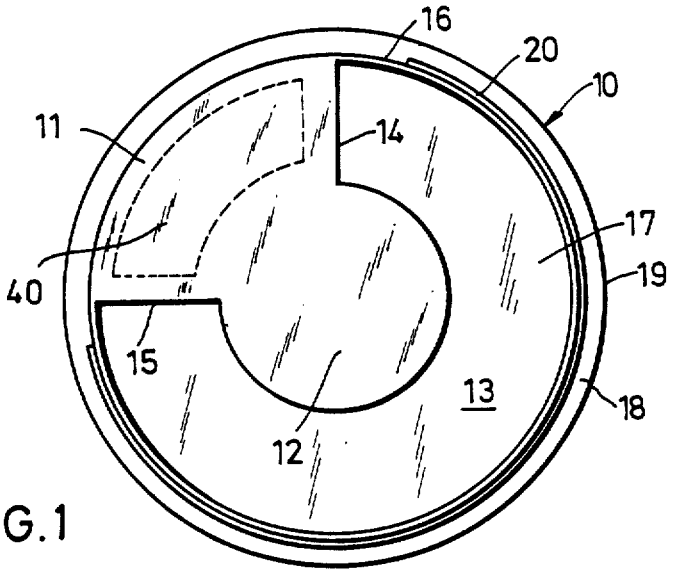
FIG. 1 shows a plan view of the open box of the dispenser.
Figure 2:
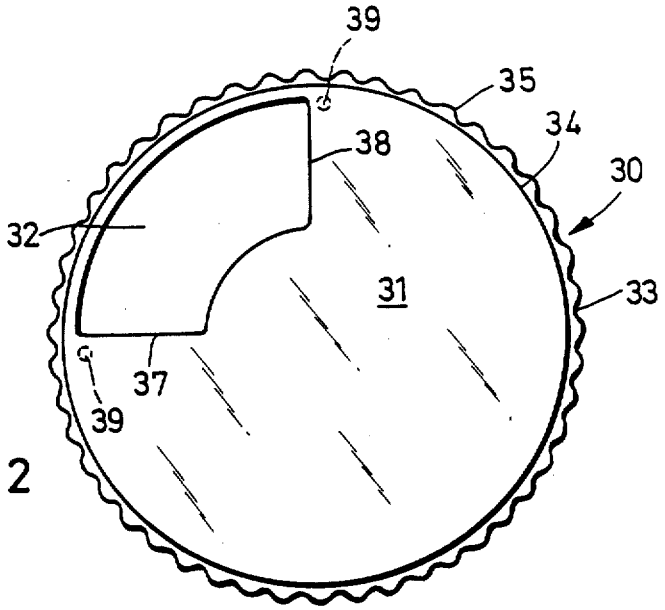
FIG. 2 shows a plan view of the cover of the dispenser.

The cavity of a circular box 10, preferably made of plastic, is divided by a packing member 11 shaped as part of a circular ring and a circular packing member 12 abutting the inner circumference of packing member 11 in such a manner that a cavity 13 shaped as part of a circular ring is formed which is especially provided to be filled with dental technical facing composition. The surfaces 14 and 15 of packing member 11, defining the ends of cavity 13, extend radially with regard to the center of the box. Into a shallow recess 40 (shown by a dotted line) on the upper side of packing member 11, a suitably cut adhesive label indicating the contents of the dispenser can be fitted. The height of both packing members 11 and 13 is substantially equal to that of the wall 16 of box 10, i.e. the flat surface of packing members 11 and 12 lies substantially at the level of the opening of the box. The bottom 17 of box 10 is flat and parallel to the plane of the opening. On the outer side of wall 16, a rectangular annular shoulder 18 is formed substantially at the level of bottom 17, while a cylindrical ring 19 opposing wall 16 extends from shoulder 18 and protrudes from bottom 17. A part of the outer circumference of wall 16 is surrounded by a rib 20 ending at a distance before both surfaces 14 and 15 of the packing member 1 shaped as part of a circular ring.

Figure 3:
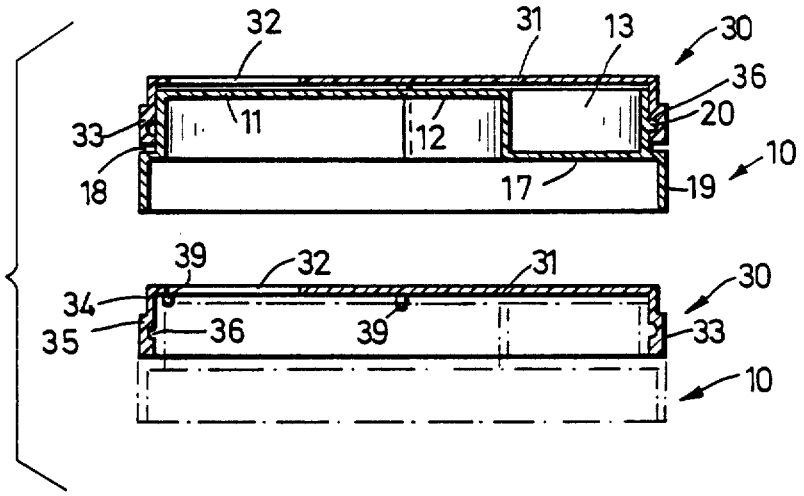
FIG. 3 illustrates a sectional view of two dispensers to be stacked, respectively consisting of a box and a cover.

As can be seen in FIG. 3, both packing members 11 and 13 are hollow and merge into one another. Their bottom sides are open as well. Bottom 17 of the cavity 13 shaped as part of a circular ring extends from the opening of both packing members 11 and 12 and ends at ring 19.

A cover 30 closing box 10 and being turnable on top thereof is also circular and is formed as a cap. In the peripheral area of a wall 31 of the cover, an opening 32 shaped as part of a circular ring is provided substantially corresponding in form to the packing member 11 shaped as part of a circular ring and being slightly smaller than this packing member 11, such that upon coinciding packing member 11 and opening 33 of the cover cap 30 is smooth at the upper peripheral area 34 joining cover wall 31. Below this peripheral area 34, the outer circumference of the cap sidewall 33 is protrudingly knurled to form a knurled ring 35 facilitating the turning of cover 30 on cap 10. On the inner surface of cap sidewall 33 there is formed a closed annular groove 36, engaging rib 20 at box wall 15, guiding cover 30 when the latter is turned and securing it from being unintentionally pulled off. The smooth peripheral area 34 of cap sidewall 33 appropriately fits into ring 19 of cover 30. Thus, any desired number of dispensers consisting of box 10 and cover 30 can be assembled to form a stack that can be separated in single dispensers by pulling it apart in axial direction.

Adjacent to side edges 37 and 38 of opening 32, which also extend radially, small projections 39 are provided at the bottom surface of cover wall 31. By abutting the side surfaces 14 and 15 of packing member 11, the projections 39 lock the closed cover 30 against turning. Thus locking effect may be easily overcome by turning the cover 30 with higher initial force.

I claim:

1. A dispenser for pasty compositions, especially facing material in dental technology and the like, comprising:

a circular box being closed by a cover and having a bottom and a wall, characterized in that in the peripheral area of the box cavity there is arranged a packing member (11), covering an opening (32) formed in the cover (30) when the cover (30) is in the closing position, and that the cover (30), being guided in an endless groove (36), can be turned on the box (10).

2. The dispenser of claim 1, wherein the outer circumference of the wall (16) of the box (10) and the inner circumference of the sidewall (33) of the cover (30) there are arranged an annular groove (36) and a projection (20), respectively, which annular groove and projection engage each other and serve as a cover guide.

3. The dispenser of claim 2, wherein the bottom (17) of the box (10) is surrounded at the underside by a protruding ring (19), and that the cover (30) comprises an upper peripheral area (34) engagable snug fit into the ring (19).

4. The dispenser of claim 2, wherein the box (10) is made of plastic, and in that both packing members (11, 12), with their surfaces arranged substantially at the level their surfaces arranged substantially at the level of the edge of the box wall (16), are molded as hollow elevations into the bottom (17) of the box (10).

5. The dispenser of claim 1 wherein the packing member (11) and the opening (32) are shaped as part of a circular ring, and the inner circumference of the packing member (11) is shaped as part of a circular ring arranged around a central circular packing member (12) surrounded by a cavity (13) shaped as part of a circular ring.

6. The dispenser of claim 5, wherein the box (10) is made of plastic, and in that both packing members (11, 12), with their surfaces arranged substantially at the level of the edge of the box wall (16), are molded as hollow elevations into the bottom (17) of the box (10).

7. The dispenser of claim 3, wherein the surfaces (14, 15) of the packing member (11), defining the ends of the cavity (13) extend radially with regard to the center of the box.

8. The dispenser of claim 7, wherein the box (10) is made of plastic, and in that both packing members (11, 12), with their surfaces arranged substantially at the level of the edge of the box wall (16), are molded as hollow elevations into the bottom (17) of the box (10).

9. The dispenser of claim 7, wherein the bottom (17) of the box (10) is surrounded at the underside by a protruding ring (19), and that the cover (30) comprises an upper peripheral area (34) engagable snug fit into the ring (19).

10. The dispenser of claim 1, wherein the box (10) is made of plastic, and in that both packing members (11, 12), with their surfaces arranged substantially at the level of the edge of the box wall (16), are molded as hollow elevations into the bottom (17) of the box (10).

11. The dispenser of claim 6, wherein the bottom (17) of the box (10) is surrounded at the underside by a protruding ring (19), and that the cover (30) comprises an upper peripheral area (34) engagable snug fit into the ring (19).

12. The dispenser of claim 1, wherein the bottom (17) of the box (10) is surrounded at the underside by a protruding ring (19), and that the cover (30) comprises an upper peripheral area (34) engagable in snug fit with the ring (19).

13. The dispenser of claim 1, wherein the cover (30) is formed as a cap, provided with a knurled ring (35) on the outer circumference of the sidewall (33) of the cap.

14. The dispenser of claim 13, wherein the bottom (17) of the box (10) is surrounded at the underside by a protruding ring (19), and that the cover (30) comprises an upper peripheral area (34) engagable snug fit into the ring (19).

15. The dispenser of claim 13, wherein at the upper circumference of the wall (16) of the box (10) and at the inner circumference of the sidewall (33) of the cover (30) there are arranged an annular groove (36) and a projection (20), respectively, which annular groove and projection engage each other and serve as a cover guide.

16. The dispenser of claim 15, wherein the bottom (17) of the box (10) is surrounded at the underside by a protruding ring (19), and that the cover (30) comprises an upper peripheral area (34) engagable snug fit into the ring (19).

17. The dispenser of claim 15, wherein the box (10) is made of plastic, and in that both packing members (11, 12), with their surfaces arranged substantially at the level of the edge of the box wall (16), are molded as hollow elevations into the bottom (17) of the box (10).

18. The dispenser of claim 15, wherein the packing member (11) and the opening (32) are shaped as part of a circular ring, and the inner circumference of the packing member (11) is shaped as part of a circular ring arranged around a central circular packing member (12) surrounded by a cavity (13) shaped as part of a circular ring.

19. The dispenser of claim 18, wherein the box (10) is made of plastic, and in that both packing members (11, 12), with their surfaces arranged substantially at the level of the edge of the box wall (16), are molded as hollow elevations into the bottom (17) of the box (10).

20. The dispenser of claim 18, wherein the surfaces (14, 15) of the packing member (11), defining the ends of the cavity (13), extend radially with regard to the center of the box.

21. The dispenser of claim 20, wherein the box (10) is made of plastic, and in that both packing members (11, 12), with their surfaces arranged substantially at the level of the edge of the box wall (16), are molded as hollow elevations into the bottom (17) of the box (10).

22. The dispenser of claim 20, wherein the bottom (17) of the box (10) is surrounded at the underside by a protruding ring (19), and that the cover (30) comprises an upper peripheral area (34) engagable in snug fit with the ring (19).

23. The dispenser of claim 13, wherein the box (10) is made of plastic, and in that both packing members (11, 13), with their surfaces arranged substantially at the level of the edge of the box wall (16), are molded as hollow elevations into the bottom (17) of the box (10).

24. The dispenser of claim 23, wherein the bottom (17) of the box (10) is surrounded at the underside by a protruding ring (19), and that the cover (30) comprises an upper peripheral area (34) engagable snug fit into the ring (19).

25. The dispenser of claim 13, wherein the packing member (11) and the opening 32 are shaped as part of a circular ring, and the inner circumference of the packing member (11) is shaped as part of a circular ring arranged around a central circular packing member (12) surrounded by a cavity (13) shaped as part of a circular ring.

26. The dispenser of claim 25, wherein the surfaces (14, 15) of the packing member (11), defining the ends of the cavity (13), extend radially with regard to the center of the box.

27. The dispenser of claim 26, wherein the box (10) is made of plastic, and in that both packing members (11, 12), with their surfaces arranged substantially at the level of the edge of the box wall (16), are molded as hollow elevations into the bottom (17) of the box (10).

28. The dispenser of claim 26, wherein the bottom (17) of the box (10) is surrounded at the underside by a protruding ring (19), and that the cover (30) comprises an upper peripheral area (34) engagable in snug fit with the ring (19).

* * * * *